(12) United States Patent
Howard

(10) Patent No.: US 10,064,750 B2
(45) Date of Patent: *Sep. 4, 2018

(54) MALE PENILE SEXUAL ENHANCEMENT DEVICE AND MEDICAL AID

(71) Applicant: Ron Howard, Sugar Land, TX (US)

(72) Inventor: Ron Howard, Sugar Land, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/443,055

(22) Filed: Feb. 27, 2017

(65) Prior Publication Data

US 2017/0165098 A1  Jun. 15, 2017

Related U.S. Application Data

(63) Continuation of application No. 14/550,377, filed on Nov. 21, 2014, now Pat. No. 9,615,960.

(51) Int. Cl.
*A61F 5/41* (2006.01)

(52) U.S. Cl.
CPC .......... *A61F 5/41* (2013.01); *A61F 2005/414* (2013.01)

(58) Field of Classification Search
CPC ... A61F 5/41; A61F 2005/411; A61F 205/414
USPC ...................................... 600/38–41
See application file for complete search history.

(56) References Cited

U.S. PATENT DOCUMENTS

| | | | | |
|---|---|---|---|---|
| 2,576,024 A | * | 11/1951 | Laser ........................ | A61F 5/41 248/95 |
| 5,244,454 A | * | 9/1993 | Coates ...................... | A61F 5/41 600/41 |
| 5,439,007 A | * | 8/1995 | Fischer ..................... | A61F 5/41 128/842 |
| 9,615,960 B2 | * | 4/2017 | Howard .................... | A61F 5/41 |

* cited by examiner

*Primary Examiner* — Samuel Gilbert

(57) ABSTRACT

An apparatus for assisting in copulation and preventing discomfort due to testicular retraction or displacement (e.g., retractile testicle) during copulation and other activities is disclosed. The apparatus substantially encompasses, circumferentially, the upper portion of the shaft of a penis without constricting the urethra area at the base of the shaft of the penis. The apparatus further conforms to the torso behind the scrotal sack (i.e., between scrotum and torso) to prevent undesired movement of testicles into the abdomen area. The apparatus has a substantial U-shape, the legs curving inwardly toward respective anchoring nodes. Anchoring nodes may be included at the end of each leg of the apparatus to assist in minimizing movement of the apparatus while in use. The apparatus may rigid or may be slightly flexible and, when in use as a copulation aid, provides pressure to restrict outflow of blood from corpora cavernosa thus assisting to maintain erection.

16 Claims, 6 Drawing Sheets

MALE PENILE SEXUAL ENHANCEMENT DEVICE AND MEDICAL AID

CROSS REFERENCE TO RELATED APPLICATIONS

This disclosure is a continuation of and claims priority to, U.S. patent application Ser. No. 14/550,377, filed 21 Nov. 2014, entitled "Male Penile Sexual Enhancement Device and Medical Aid," by inventor Ron Howard, which is incorporated by reference in its entirety for all available purposes.

TECHNICAL FIELD OF THE INVENTION

The present disclosure relates generally to an apparatus to assist in copulation and prevent undesired movement or displacement of the testicles. More particularly, this disclosure relates to an apparatus that circumferentially encompasses the upper portion of a penis at the juncture with the torso (i.e., at the base of penis) and includes contoured extensions to fit between the scrotal sack and the torso.

BACKGROUND

Referring to FIG. 1A, view 100 illustrates a cross-sectional view of the human penis. The human penis contains at least three cylinders (e.g., 105, 110 and 115) encased in a sheath 120. Sheath 120 is called the bucks fascia or deep fascia of the penis. The three cylinders are the corpus spongiosum 115 and two corpus cavernosum penis (i.e., 105 and 110). The function of the corpus spongiosum 115 in erection is to prevent the urethra 116 from pinching closed, thereby maintaining the urethra 116 as a viable channel for ejaculation. To do this, the corpus spongiosum 115 remains pliable during erection while the two corpus cavernosum penis (105 and 110), which are collectively referred to as the corpora cavernosa, become engorged with blood. The two corpus cavernosum penis (105 and 110) each contain spongy erectile tissue. Cavernosal arteries (106 and 111) run along the middle of each corpus cavernosum penis (105 and 110). The function of the corpus cavernosum penis (105 and 110) is purely erectile. Muscles surround the corpus cavernosum penis (105 and 110) and spongiosum 115. Generally, in the male penis, an erection is produced when arterial blood flows to the erectile tissues of the penis, but the veinal return flow of blood to the body is restricted so that the erectile tissues become filled or engorged with blood. The restriction is normally performed by sphincter muscles (not shown in FIG. 1) which function in response to sexual arousal. Some men have various problems, e.g., advancing age, physiological or psychological problems, or premature relaxation prior to completion of coitus. This may lead to these men and/or their partner being unsatisfied with their performance during sex. It is noted that the veinal return flow of blood (i.e., outflow from each corpus cavernosum penis 105 and 110) to the body is accomplished, at least in part, by blood flowing in veins (e.g., superficial dorsal vein 125 and deep dorsal vein 126) located near the outer circumference of the penis. These sphincter muscles and other muscles work together to physically and functionally support the penis when erect and then gradually contract after ejaculation. To achieve erection the brain sends impulses to the nerves in the penis to cause the multiple muscles around each corpus cavernosum penis (105 and 110) to relax. This allows blood to flow, in part via cavernosal arteries (106 and 111), into the open spaces inside each respective corpus cavernosum penis (each of 105 and 110). This blood creates pressure making the penis expand which then compresses the veins (e.g., 125 and 126) that normally allow blood to drain. Once the blood is trapped, a muscle (not shown) located in the corpus cavernosum penis (each of 105 and 110) helps to sustain the erection. An erection is reversed once the muscles in the penis contract preventing further blood flow into corpus cavernosum penis (105 and 110) and allowing veinal return flow of blood through veins 125, 126 and other veins (not shown) to the body from each corpus cavernosum penis (105 and 110).

Retractile testicle is a medical condition affecting mostly young children but can also be a problem for mature adult men. Retractile testicle refers to a condition where one or even two testicles may move back and forth between the scrotal sack and the groin. When the testicle is in the groin region it may cause discomfort or even pain and may have to be manipulated by hand to return it to its proper location in the scrotal sack. Obviously, it would be undesirable to have a testicle retract during sexual intercourse. Sometimes the retracted testicle cannot be moved back to its proper location in the scrotal sack and medical intervention may be required. This condition is sometimes referred to as an ascending testicle.

The position of one testicle is usually independent of the position of the other testicle. That is, they may migrate independently. Retractile testicle is different from an undescended testicle, an undescended testicle is a medical condition known as cryptorchidism. The undescended testicle is one that has never properly entered the scrotal sack. Undescended testicles are not pertinent to this disclosure and will not be discussed further.

The cremaster muscle is a thin pouch-like muscle in which each testicle rests. An overactive muscle may cause a testicle to become a retractile testicle. When the cremaster muscle contracts, it pulls the testicle up toward the body. Alternatively, even without retraction of the cremaster muscle, certain movements or positions during sexual intercourse may cause a testicle to retract and cause a disruption to the intercourse. The main purpose of the cremaster muscle is to control the temperature of the testicle. In order for a testicle to develop and function properly, it needs to be slightly cooler than normal body temperature. When the environment is warm, the cremaster muscle should be relaxed; when the environment is cold, the cremaster muscle contracts and draws the testicle toward the warmth of the body. The cremaster reflex may also be stimulated by rubbing the genitofemoral nerve on the inner thigh or by extreme emotion, such as anxiety. If the cremaster muscle is strong enough, it may cause a retractile testicle by pulling the testicle up out of the scrotal sack and into the groin.

Prior art devices include "cock-rings" and other tourniquet type devices that completely encircle the penis and constrict blood circulation in the penis in an attempt to sustain an erection. However, penile constrictor rings and other tourniquet type devices are subject to certain well known disadvantages. First, they may be difficult to use because of application issues and timing of application such as having to be applied before an erection occurs. Second, they may be dangerous to use, in that if left in place too long, they may result in permanent damage to the penis because of restricted circulation. Third, if applied and fully operative at the moment of orgasm and ejaculation, they may interfere and reduce the pleasurable sensations of orgasm and ejaculation or even inhibit ejaculation altogether by constriction of the urethra 116 prohibiting the natural passage of bodily fluids. Further, tourniquet type devices, penile rings, and other prior art devices do not take into consideration a retractile testicle condition in any manner. To address all of these and other issues, the disclosed apparatus, in one embodiment, performs multiple functions and has several attributes that are explained further below to assist a male in his performance, enjoyment and comfort during sexual intercourse.

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings. For clarity, not all reference numerals will be repeated in conjunction with each of the drawings. Unless otherwise stated, directional terms (e.g., left, right top, bottom) used to discuss the disclosed apparatus are from the perspective of a person wearing the device. Additionally, like reference numerals in the drawings identify identical or substantially similar elements, wherein:

NOTATION AND NOMENCLATURE

Certain terms are used throughout the following description and claims to refer to particular components and configurations of an apparatus. As one skilled in the art will appreciate, the same component may be referred to by different names. This document does not intend to distinguish between components that differ in name but not function. In the following discussion and in the claims, the terms "including" and "comprising" are used in an open-ended fashion, and thus should be interpreted to mean "including, but not limited to . . . "

Figure 8:
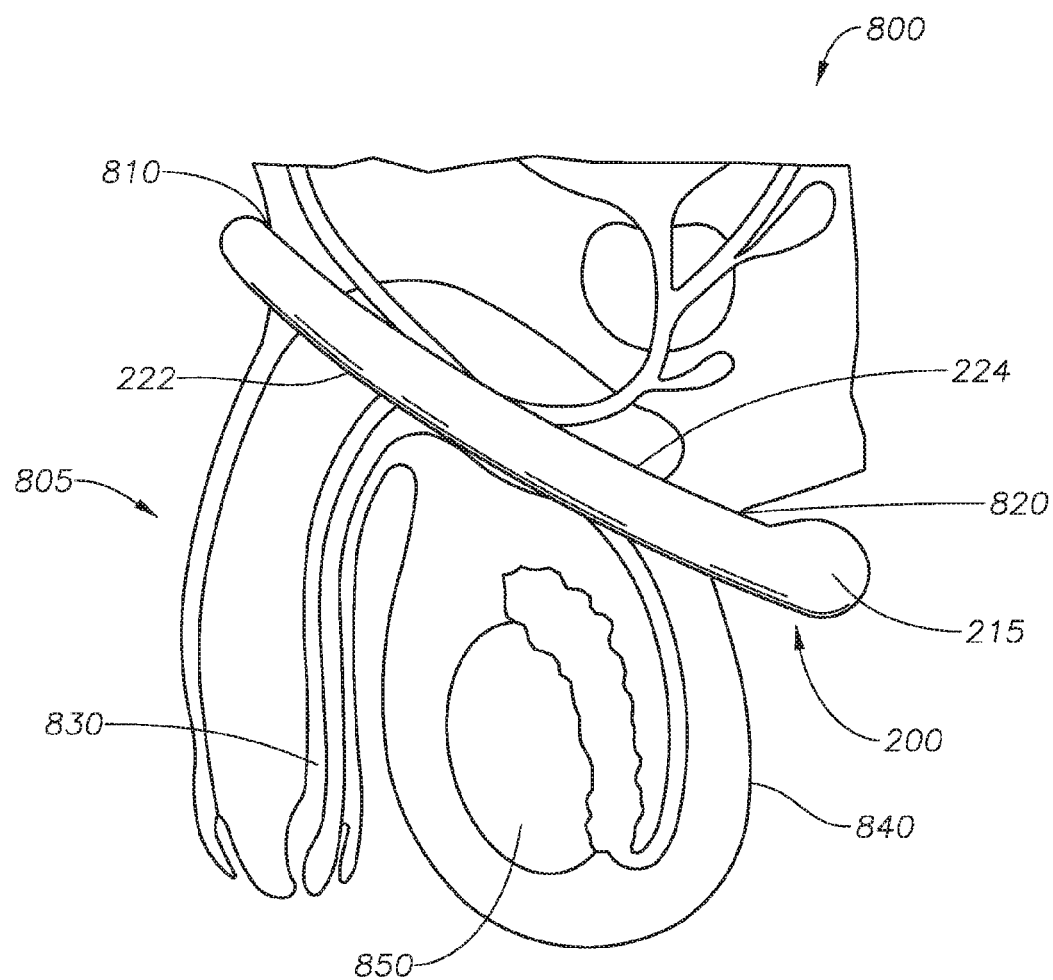
FIG. 8 illustrates an orientation of apparatus 200, with respect to male genitalia, in an operative position in accordance with some embodiments of the present disclosure.

This disclosure describes embodiments of an apparatus 200 configured in the form of a substantially U-shape member to both constrict a portion of the outer circumferential portion of the penis and restrict movement of one or both testicles to ensure they stay within the scrotal sack. In use, apparatus 200 is an inverted U-shape from the perspective of the wearer as will be made clear in the following description. FIG. 8 shows such an apparatus 200 and selected relevant portion of the male anatomy, with apparatus 200 being shown in the orientation in which it would be worn. FIG. 8 shows the left side of apparatus 200. The directional terms "left," "right," "front," "rear," "below," "behind" and the like are used herein from the point of view of one wearing apparatus 200. Thus, e.g., FIG. 8 shows the left side of apparatus 200. Furthermore, while "front" refers to the side directed away from the body and "rear" refers to the side directed toward the body, as seen in FIG. 8 the "front" of apparatus 200 is also directed downward in the figure while the "rear" of the apparatus is also directed upward in the figure. One benefit of the disclosed apparatus is to facilitate and maintain an erection through partial constriction of the penis and another benefit is to deter if not prevent movement of a testicle from the scrotal sack back into the body. For purposes of this disclosure, prevention of movement of a testicle from the scrotal sack back into the body will refer to prevention of movement of a testicle from the scrotal sack into the "groin region." The groin region may also be referred to as the abdomen in other literature; however, the term groin region will be used to indicate an undesirable location of the one or two testicles when they are not properly positioned within the scrotal sack. Additionally, when reference is made to the "torso" of the body, it is understood that the torso of the body does not include the scrotum or scrotal sack and it would be undesirable for a testicle to migrate from the scrotal sack to any part of the body inside the torso. The "torso" will be understood to include the groin region and inner thigh portions of both the left and right legs.

DETAILED DESCRIPTION

The foregoing description of the figures is provided for the convenience of the reader. It should be understood, however, that the embodiments are not limited to the precise arrangements and configurations shown in the figures. Also, the figures are not necessarily drawn to scale, and certain features may be shown exaggerated in scale or in generalized or schematic form, in the interest of clarity and conciseness. The same or similar parts may be marked with the same or similar reference numerals.

While various embodiments are described herein, it should be appreciated that the present disclosure encompasses many inventive concepts that may be embodied in a wide variety of contexts. The following detailed description of example embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. For example, the two distinct benefits of this disclosure may be accomplished without a single integral apparatus The scope of the invention is defined by the appended claims and equivalents thereof. Illustrative embodiments of the invention are described below. In the interest of clarity, not all features of an actual implementation are described in every embodiment disclosed in this specification. In the development of any such actual embodiment, numerous implementation-specific decisions may need to be made to achieve the design-specific goals, which may vary from one implementation to another. It will be appreciated that such a development effort, while possibly complex and time-consuming, would nevertheless be a routine undertaking for persons of ordinary skill in the art having the benefit of this disclosure.

Figure 1A:
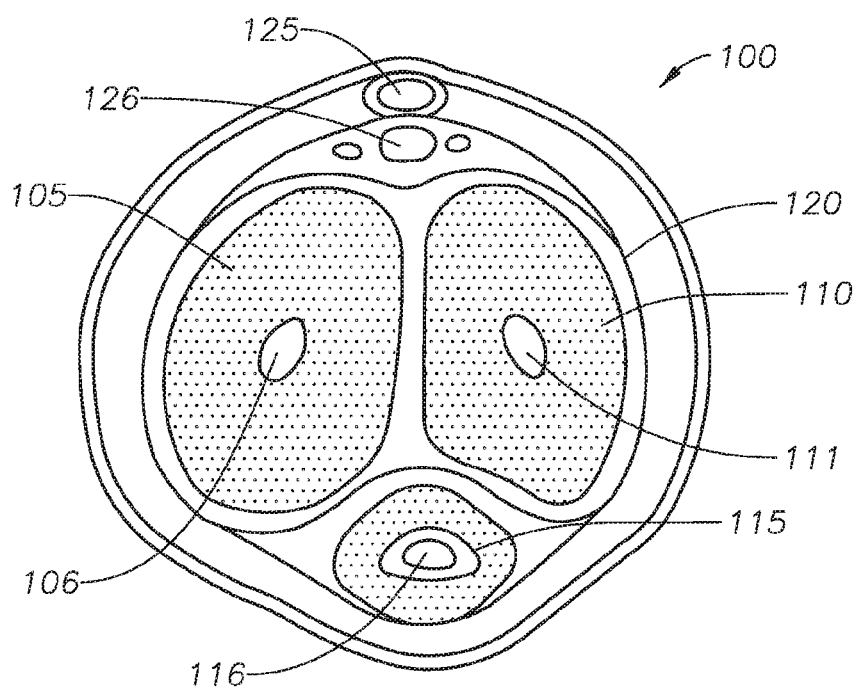
FIGS. 1A-B illustrate a cross-sectional view 100 of a human penis.
Figure 1B:
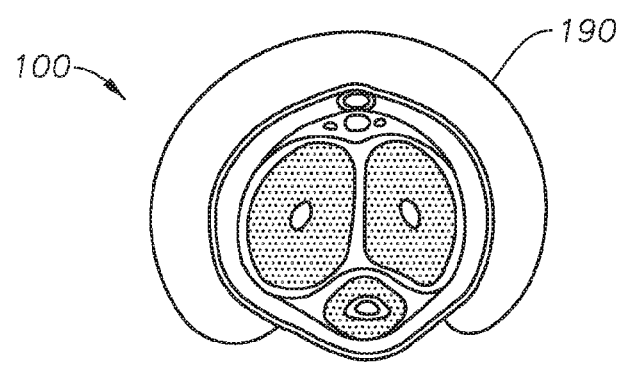

The present disclosure relates generally to an apparatus to assist in copulation and prevent undesired movement or displacement of the testicles. More particularly, this disclosure relates to an apparatus that circumferentially encompasses the upper portion of a penis at the juncture with the torso (i.e., at the base of penis). The disclosed apparatus further includes contoured extensions to fit between the scrotal sack and the torso such that the apparatus applies a squeezing type pressure on any superficial veins (not shown), the dorsal veins of the penis (e.g., veins 125 and 126 of FIG. 1A), and the corpus cavernosum penis erectile tissues located on each side of the penis shaft (e.g., elements 105 and 110 of FIG. 1). Disclosed apparatus 200 therefore may be configured to assist in maintaining placement of the testicles in the scrotal sack by preventing their retraction into the abdomen region. Disclosed apparatus 200 is configured, in some embodiments, to perform at least four functions to enhance sexual intercourse and testicular control for the male partner wearing apparatus 200. These four functions include, but are not limited to, 1) assisting in obtaining and maintaining an erection; 2) reducing or eliminating the condition referred to as retractile testicle; 3) permitting the natural passage of bodily fluids, at least in part because unlike penile rings or other tourniquet type devices, the disclosed apparatus does not constrict the urethra 116; and 4) because the disclosed apparatus only applies pressure on the erectile tissues of the penis during sexual arousal, the disclosed apparatus allows for normal evacuation of blood upon relaxation of the penis and can thus be worn for extended time periods to control a retractile testicle.

Figure 2:
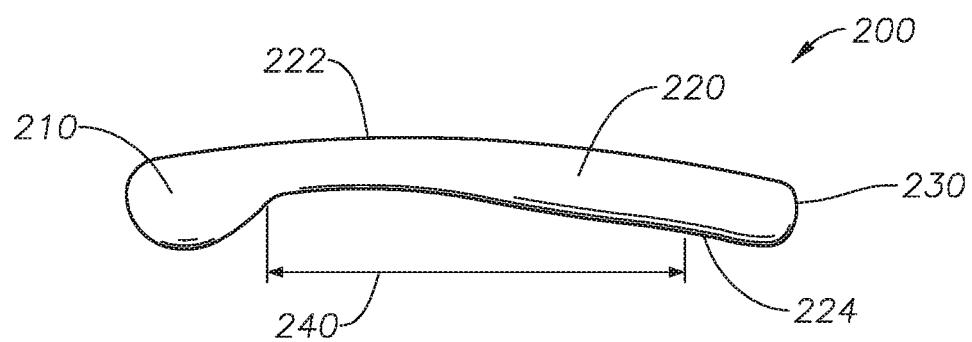
FIG. 2 illustrates a left-side view of apparatus 200, in accordance with some embodiments of the present disclosure.

Referring now to FIG. 2, apparatus 200 is shown from a view of the left side of the apparatus. It will be noted that apparatus 200 in FIG. 2 is shown in an orientation with its front facing upward and thus the orientation of FIG. 2 is substantially upside down from that shown in FIG. 8. Apparatus 200 has a top portion identified by reference number 230 located at the apex of the substantially U-shaped member, a left-side arc at element 220 and a left anchoring node as indicated by reference number 210. Apparatus 200 has a front facing side 222 and a rear facing side 224, seen also in FIG. 8. Front facing side 222 and rear facing side 224 are named relative to how apparatus 200 would be worn in use. Thus, rear facing side 224 would be toward the torso (and groin region) of the person wearing apparatus 200 (and also angled upward, as seen in FIG. 8) and front facing side 222 would be facing away, in a frontward direction, from the person wearing apparatus 200 (and also angled downward, as seen in FIG. 8). Apparatus 200, as shown in FIG. 2, also has a torso-arc as illustrated by the region defined by element 240. The torso-arc 240 is along rear facing side 224 and may be made so as to conform to the contour of the torso of the body while apparatus 200 is in use. That is, torso-arc 240 curves inward toward the torso of the person wearing apparatus 200. Apparatus 200 will generally also curve around the base (or root) of the penis and each anchoring node (e.g., 210) will be behind the scrotal sack and between the scrotal sack and the torso, as shown in FIG. 8.

Figure 3:
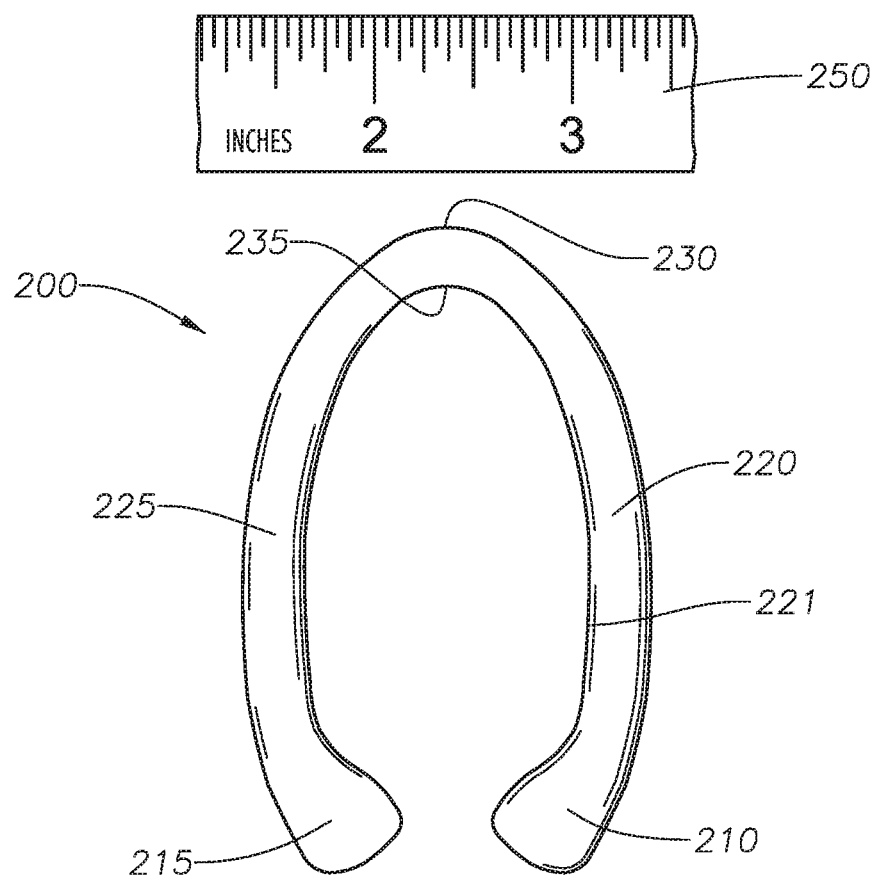
FIG. 3 illustrates a front facing view of apparatus 200, in accordance with some embodiments of the present disclosure.
Figure 4:
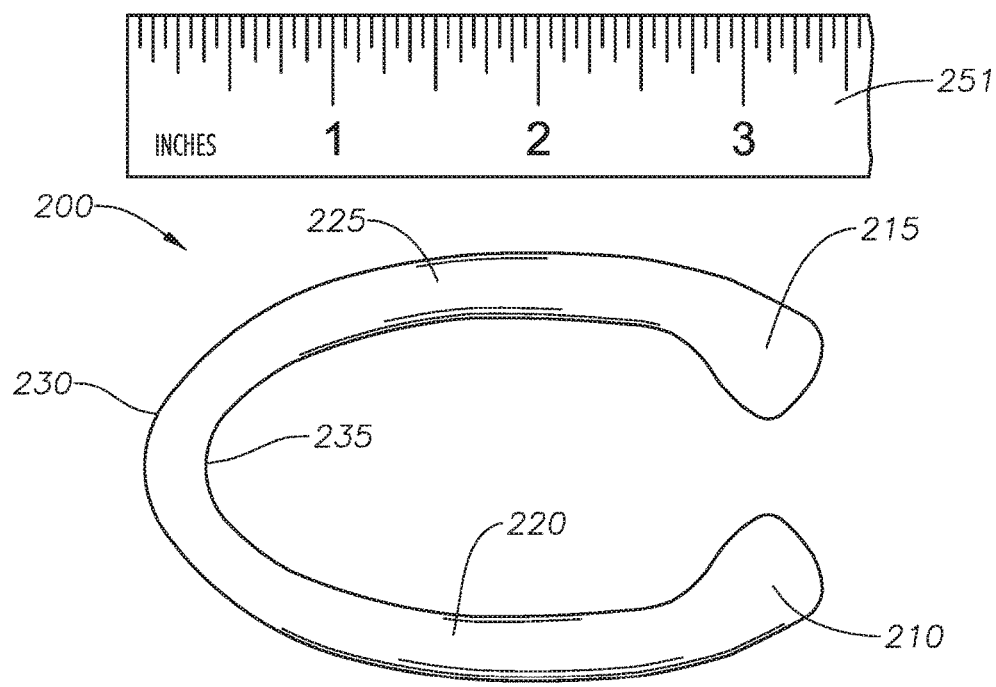
FIG. 4 illustrates a rear view of apparatus 200, in accordance with some embodiments of the present disclosure.

FIG. 3 illustrates a front view of apparatus 200 and provides a portion of a ruler 250 to indicate approximate scale for one example embodiment. It will be noted that many different sizes of apparatus 200 may be manufactured to adapt to different size males and may optionally be custom fit and/or built to order to achieve optimal results. Different sizes of apparatus 200 may allow for varying degrees of pressure to be applied to either an erect or a non-erect penis. Further, as the penis becomes erect, pressure applied by apparatus 200 may increase. In one embodiment, little or no pressure is applied to a non-erect penis and pressure will begin to be applied and increase as the corpus cavernosum penis (each of 105 and 110) fill with blood. FIG. 3 also introduces top inner portion 235, right-side arc 225, and right side anchoring node 215 of apparatus 200. Left-side arc 220 and right side arc 225 may be configured to extend beyond a region of pressure applied by apparatus 200 to a penis and curve behind and apply a squeezing type pressure to the top portion of the scrotal sack to reduce movement of testicles. In one embodiment, anchoring nodes 210 and 215 are at least beyond a region of penile pressure applied by apparatus 200 in the direction of the gap or opening between respective ends of each arc element 220 and 225. Although anchoring nodes 210 and 215 are illustrated at the terminal ends of their respective side arcs, it is possible that anchoring nodes 210 and 215 may be placed at an appropriate midpoint (e.g., midpoint 221, not necessarily at the exact middle of arc element 220 or 225) along each arc with a portion of each arc extending beyond its corresponding anchoring node. This extension portion (not shown in the figures) for each arc may be formed as a continuation of the arc angle or continue at a lesser or greater angle. For example, the extension portion (not shown) may increase in angle (i.e., curve more sharply) and further curve around and behind the scrotal sack. Note also, in the embodiment of FIG. 3, anchoring nodes 210 and 215 protrude from the rear facing side 224 of their respective side arc (e.g., 220 and 225).

Figure 5:
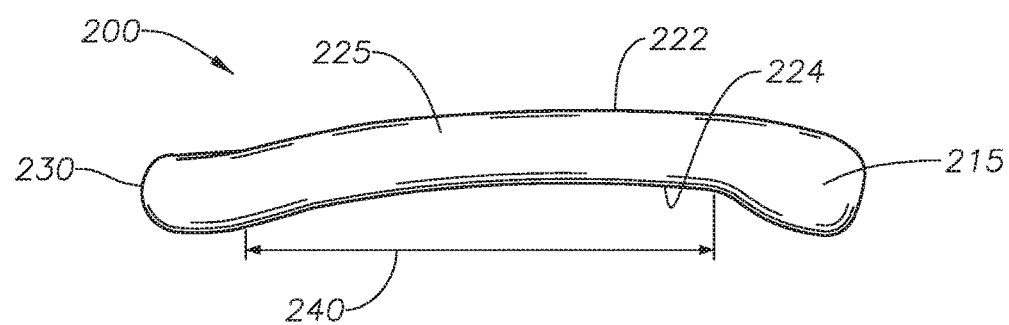
FIG. 5 illustrates a right-side view of apparatus 200, in accordance with some embodiments of the present disclosure.
Figure 6:
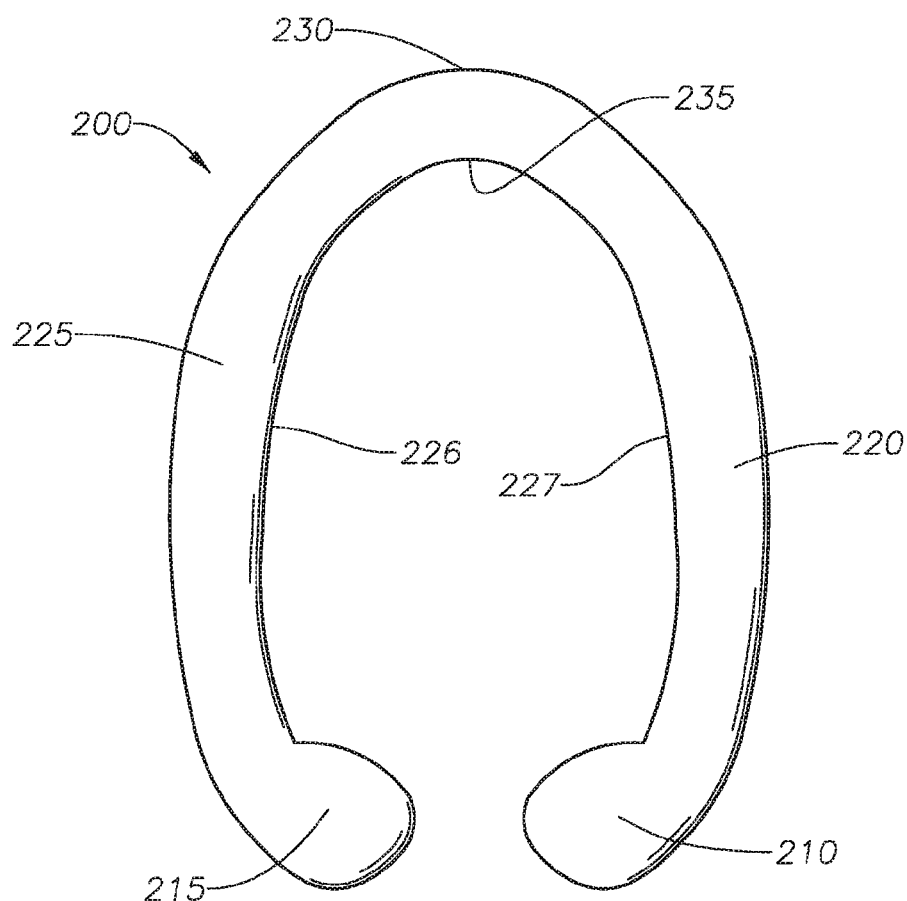
FIG. 6 illustrates a second front facing view of apparatus 200, in accordance with some embodiments of the present disclosure.
Figure 7:
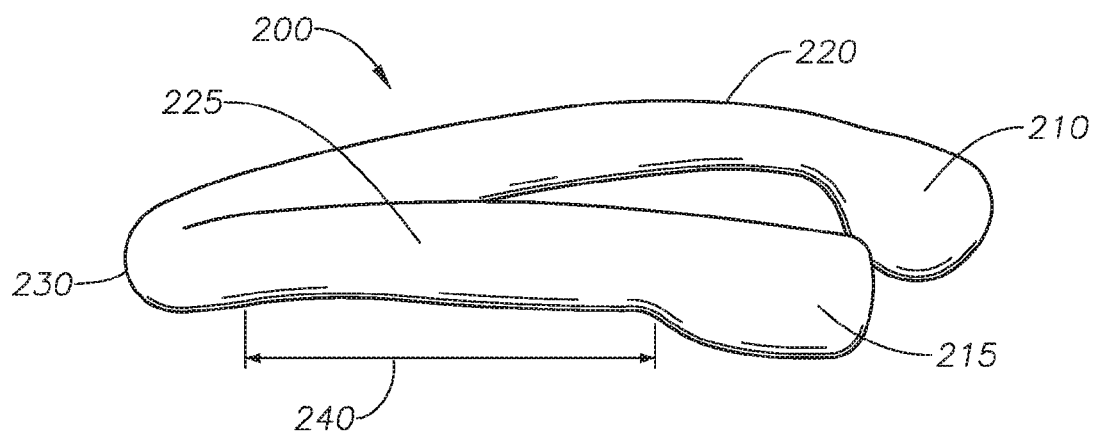
FIG. 7 illustrates a side view at an angle of apparatus 200, in accordance with some embodiments of the present disclosure.

Referring now to FIGS. 4-7, FIG. 4 illustrates a rear-view of apparatus 200 and shows a portion of a ruler 251 to indicate approximate scale for one example embodiment. FIG. 5 illustrates a view from the right side of apparatus 200 and shows elements from a right view perspective analogous to those described above for FIG. 2. FIG. 6 illustrates a second front facing view of apparatus 200 and introduces elements 226 and 227. Element 226 is to roughly indicate a point on the inside of right-side arc 225 and element 227 is to roughly indicate a corresponding point on the inside of left-side arc 220. The region from the top inner portion 235 to point 226 and the region from top inner portion 235 to point 227 indicate regions where pressure from each inner arc portion would be applied to a penile shaft when apparatus 200 is in use. Obviously, different users would have slightly different points where pressure from each inner arc would end because of different size penises, so the locations of 226 and 227 are approximate. FIG. 7 illustrates a side view at an angle of apparatus 200, in accordance with some embodiments of the present disclosure. In FIG. 7 the continued curvature of side arcs 220 and 225 toward anchoring nodes 210 and 215 (which in this example are at an endpoint of each respective side arc) in addition to torso arc 240 can be seen. To clarify, the curvature of the side arcs 220 and 225 is seen as in FIG. 7 as a curvature between foreground and background, while the torso arc 240 is seen in FIG. 7 as a curvature between top and bottom; in FIGS. 2, 5 and 8 only the torso arc 240 curvature can be seen, while in FIGS. 3, 4, and 6 only the side arc curvature can be seen. As explained above, if anchoring nodes (e.g., 210 and 215) are at a midpoint (e.g., 221) curvature of side arcs 220 and 225 may continue past each anchoring node (e.g., 210 and 215).

Referring now to FIG. 8, view 800 illustrates apparatus 200 in its operative (i.e. worn) position with point 810 illustrating the base of a non-erect penis 805 that corresponds to inner top 235 of apparatus 200. Point 820 of FIG. 8 illustrates where the scrotal sack 840 attaches to a male groin region. Note that anchoring nodes 210 and 215 maintain a position beneath point 820 such that the scrotal sack 840 is slightly gripped to deter or prevent movement of one or more testicles 850 toward the groin region and to prevent slippage of apparatus 200. As explained throughout this disclosure, apparatus 200 is configured to apply circumferential pressure to the upper portion and two side portions of penis 805, where the upper portion includes the superficial dorsal vein (125 in FIG. 1) and deep dorsal vein (126 in FIG. 1) and the two side portions include corpus cavernosum penis (105 and 110 in FIG. 1). One of ordinary skill in the art will recognize that the phrase "the upper portion and two side portions including corpus cavernosum penis" as used in this disclosure refers generally to the area of penis 805 to the left of urethra 830 as shown in FIG. 8. Note urethra 830 is the same as urethra 116 shown in cross-sectional view 100 of FIG. 1. The gap between respective ends of side arcs 220 and 225 of apparatus 200 (not shown in FIG. 8) is adapted to position below and behind a bottom portion of penis 805 so that side arcs 220 and 225 do not cause substantial constriction at the bottom portion of penis 805. The bottom portion of penis 805 is generally the area of penis 805 to the right of and including urethra 830 as shown in FIG. 8. To be clear, reference is made to FIG. 1B to explain that "the upper portion and two side portions including corpus cavernosum penis," where apparatus 200 provides circumferential pressure, generally refers to the area outlined circumferentially by element 190 in FIG. 1B, while the "bottom portion of the penis" generally refers to the area not outlined circumferentially by element 190 in FIG. 1B. It may be noted that while the directional terms "upper," "bottom," etc. are clearly reflected in FIG. 1B, in contrast, because FIG. 8 shows a non-erect rather than an erect penis, the "upper portion" appears on the left side and the "bottom portion" appears on the right side in FIG. 8.

This disclosure may include descriptions of various benefits and advantages that may be provided by various embodiments. One, some, all, or different benefits or advantages may be provided by different embodiments. For example, apparatus 200 may have different degrees of flexibility or rigidity and may be manufactured from a multitude of materials including but not limited to rubber, plastic, fiberglass, or any of a variety of metals, such as, stainless steel, chromed steel, aluminum, etc. Apparatus 200 may be made from a single material or multiple materials configured to collectively perform the disclosed benefits. In one example, apparatus 200 may be formed of a single shaped piece of plastic, formed, at least in part, by using a plastic extrusion process. In another example, a metal covered in a layer of rubber material may allow the metal material to provide structure and the rubber (or similar material) portion to provide comfort and grip. Apparatus 200 may be smooth or textured on its different surface areas. Texture may provide added benefit in function and feel or may simply provide aesthetic appeal. One example of texture enhancing function may be an enhanced grip on the person wearing apparatus 200. As used in this disclosure, a material that is flexible but inelastic refers to a material that is not completely rigid and thus allowed to bend slightly but does not stretch and retract like, for example, a rubber band. A rigid material refers to a material that will either break or conform to a new shape after enough pressure is applied. For example, a rigid and non-bendable material may be glass which would hold its shape until a breaking force is applied. Alternatively, a rigid material may also be a bendable metal that would take on a new shape and not return on its own to its original shape after bending. Thus, a rigid and bendable material utilized to manufacture apparatus 200 may include a bendable metal that may be bent after purchase to be appropriately sized by a user. Clearly, if apparatus 200 were built from a rigid but bendable material, it would be desirable to require sufficiently more force to bend apparatus 200 than apparatus 200 is expected to encounter during use because apparatus 200 should substantially maintain its shape while in use.

Figure 9:
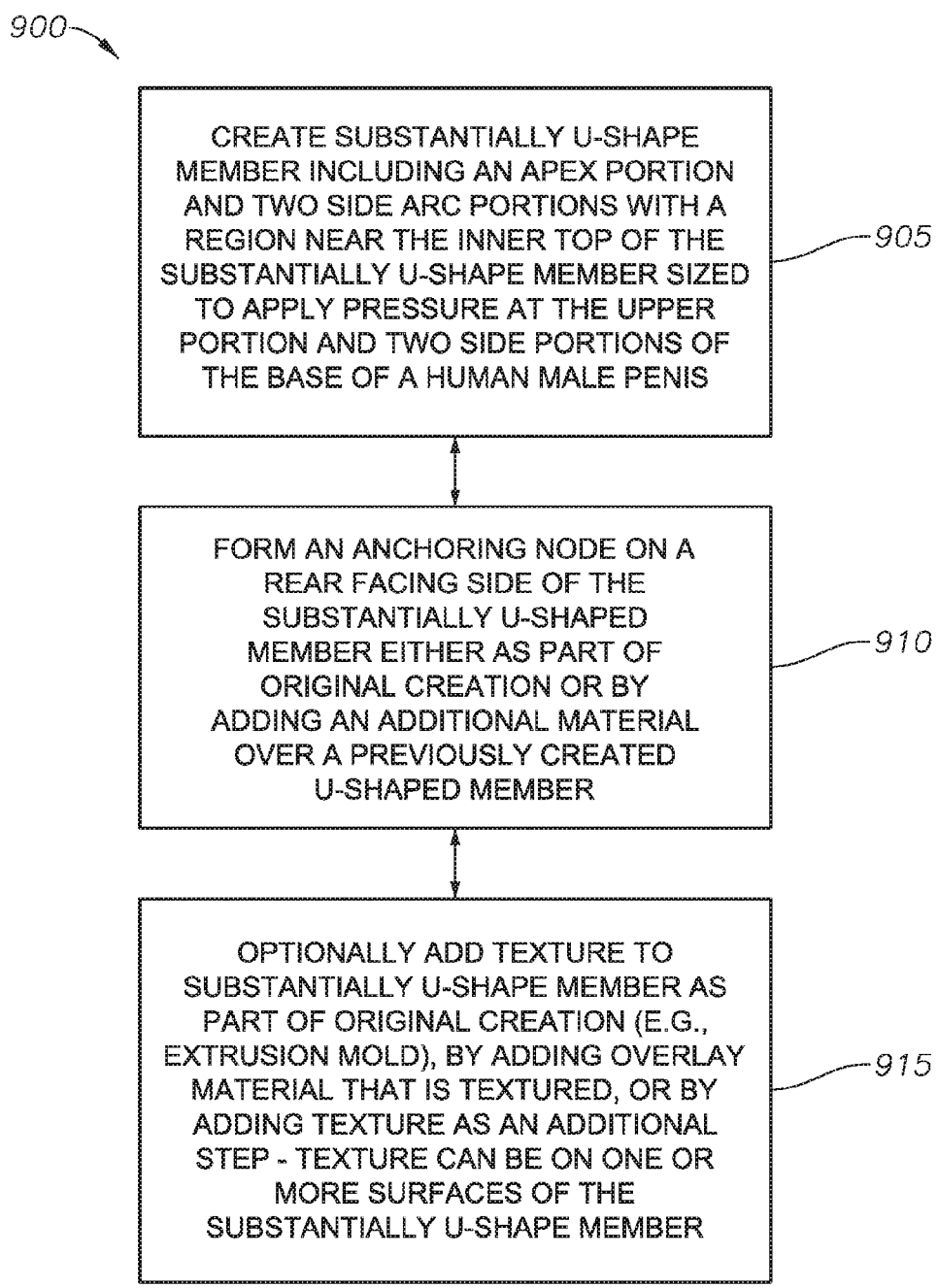
FIG. 9 illustrates a flow chart 900 describing a possible method of manufacture of apparatus 200 in accordance with some embodiments of the present disclosure.

Referring now to FIG. 9, process 900 illustrates a possible method of manufacture for an apparatus according to disclosed embodiments, such as apparatus 200. As will be clear to those of ordinary skill in the art there are many different manufacturing processes that may be used to form an apparatus according to disclosed embodiments and this simplified process flow is merely one example with several optional steps. Beginning at block 905, a substantially U-shaped member is created by forming a material in an appropriate shape in accordance with this disclosure. The forming process may consist of a single step or a combination of steps to result in an apparatus, such as apparatus 200, in conformance with disclosed embodiments. Obviously, a choice of material to form the substantially U-shaped member may causes changes to a manufacturing process. At block 910, anchoring nodes (e.g., 210 and 215) may be added to an already formed substantially U-shaped member using an overlay material. Clearly, anchoring nodes (210 and 215) may have been formed at the same time as forming the substantially U-shaped member, for example, by using an extrusion mold. At block 915, a texture may be optionally added to one or more surfaces of the substantially U-shaped member if texture is desired and if texture was not already present from original creation or on the overlay material. It will be noted that the order of steps of process 900 may be altered in a number of ways. For example, forming the substantially U-shape may take place as a final step by bending a material or composite of materials that already have some attributes of the disclosed apparatus into the substantially U-shaped member.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A method of assisting in prevention of retractile testicle, comprising:
 positioning an apparatus to be worn by a human being endowed with a torso, a scrotal sack, and a penis, the torso comprising a groin region, the scrotal sack comprising testicles, and the penis comprising a base adjoining the torso, an upper portion including a superficial dorsal vein and a deep dorsal vein, two side portions including corpus cavernosum penis, and a bottom portion including a urethra, the apparatus comprising:

a U-shaped member comprising a closed apex portion and two side arc portions and defining an opening opposite the closed apex portion, each of the two side arc portions comprising a rear-facing side adapted to face toward the torso, a front-facing side adapted to face away from the torso, and an interior region configured to apply pressure circumferentially on the upper portion and the two side portions of the penis when the penis is erect to form a penile pressure portion, the interior region being further configured to wrap around the scrotal sack between the testicles and the groin region to apply constricting pressure to the scrotal sack and impede retraction of said testicles out of the scrotal sack, so as to maintain said opening opposite said closed apex portion, with said opening being situated behind the scrotal sack at a location where said scrotal sac attaches to said groin region wherein said positioning comprising encasing the base of the penis within the interior region of the U-Shaped member and situating each of the two side arc portions between the scrotal sack and the torso of the human being.

2. The method of claim 1, wherein said positioning comprises sliding the U-Shaped member down over said upper portion of the penis along the torso behind the scrotal sack.

3. The method of claim 1, wherein said positioning comprises bending a material around the penis and behind the scrotal sack to form the U-shaped member.

4. The method of claim 1, further comprising assisting in maintenance of an erection at least in part by said penile pressure portion applying pressure to the penis to affect blood flow of the penis.

5. The method of claim 4, further comprising constricting blood flow out of the penis through application of pressure by the penile pressure portion.

6. The method of claim 1, further comprising providing an anchoring node on each of the two side arc portions of the U-Shaped member, each said anchoring node being adapted to be positioned in contact with the torso behind the scrotal sack.

7. The method of claim 6, further comprising disposing each said anchoring node at an end of each side arc portion directly adjacent the opening.

8. An apparatus configured to prevent retractile testicle, the apparatus to be worn by a human being endowed with a torso, a scrotal sack, and a penis, the torso comprising a groin region, the scrotal sack comprising testicles, and the penis comprising a base adjoining the torso, the apparatus comprising:

a U-shaped member comprising a closed apex portion and two side arc portions and defining an opening opposite the closed apex portion, each of the two side arc portions comprising a rear-facing side adapted to face toward the torso, a front-facing side adapted to face away from the torso, and an interior region defining a penile pressure portion of said U-shaped member configured to apply pressure circumferentially around the base of the penis and the scrotal sack; and an anchoring node on the rear facing side of each said side arc portion, each said anchoring node being disposed at least beyond the penile pressure portion in a direction of the opening and being configured to be positioned behind the scrotal sack, wherein the U-shaped member is configured to surround an upper portion of the penis at the base of the penis closely adjacent to the torso without constricting a bottom portion of the penis, such that the opening is positioned behind the scrotal sack, wherein each of the two side arc portions is configured to curve inward behind the scrotal sack and to apply squeezing pressure to the scrotal sack so as to assist in preventing retraction of the testicles into the groin region and in retaining the testicles in the scrotal sack, and wherein the opening opposite the closed apex portion is configured to maintain a gap in the U-shaped member.

9. The apparatus of claim 8 wherein the apparatus is configured to prevent retractile testicle during sexual intercourse.

10. An apparatus configured to assist in prevention of retractile testicle of a human being endowed with a torso, a scrotal sack, and a penis, the torso comprising a groin region, the scrotal sack comprising testicles, and the penis comprising a base adjoining the torso, an upper portion including a superficial dorsal vein and a deep dorsal vein, two side portions including corpus cavernosum penis, and a bottom portion including a urethra, the apparatus comprising:

a U-shaped member comprising a closed apex portion and two side arc portions and defining an opening opposite the closed apex portion, each of the two side arc portions comprising a rear-facing side adapted to face toward the torso, a front-facing side adapted to face away from the torso, and an interior region configured to apply pressure circumferentially on the upper portion and the two side portions of the penis when the penis is erect to form a penile pressure portion, the interior region being further configured to wrap around the scrotal sack between the testicles and the groin region to apply constricting pressure to the scrotal sack and impede retraction of said testicles out of the scrotal sack, so as to maintain said opening opposite said closed apex portion, with said opening being situated behind the scrotal sack at a location where said scrotal sac attaches to said groin region;

wherein said apparatus encases the base of the penis within the interior region of the U-Shaped member and situates each of the two side arc portions between the scrotal sack and the torso of the human being.

11. The apparatus of claim 10, wherein said U-Shaped member is adapted to slide down over said upper portion of the penis along the torso behind the scrotal sack.

12. The apparatus of claim 10, wherein said apparatus is adapted to bend around the penis and behind the scrotal sack to form the U-shaped member.

13. The apparatus of claim 10, wherein said penile pressure portion is configured to apply pressure to the penis to affect blood flow of the penis thereby assisting in maintenance of an erection.

14. The apparatus of claim 13, wherein said penile pressure portion is configured to constrict blood flow out of the penis through application of pressure thereto.

15. The apparatus of claim 10, further comprising an anchoring node on each of the two side arc portions of the U-Shaped member, each said anchoring node being adapted to be positioned in contact with the torso behind the scrotal sack.

16. The apparatus of claim 15, wherein the anchoring node for each of the two side arc portions is positioned at an end of each side arc portion directly adjacent the opening.

* * * * *